US008870802B1

(12) United States Patent
Anderson et al.

(10) Patent No.: US 8,870,802 B1
(45) Date of Patent: Oct. 28, 2014

(54) TRACTION SPLINT

(75) Inventors: Ryan L. Anderson, Detroit Lakes, MN (US); Donald O. Larson, Audubon, MN (US)

(73) Assignee: Water Crest Industries LLC, Audubon, MN (US)

( * ) Notice: Subject to any disclaimer, the term of this patent is extended or adjusted under 35 U.S.C. 154(b) by 725 days.

(21) Appl. No.: 13/085,626

(22) Filed: Apr. 13, 2011

(51) Int. Cl.
*A61F 5/00* (2006.01)

(52) U.S. Cl.
USPC .............................................. 602/32; 602/36

(58) Field of Classification Search
USPC ........ 128/846, 869, 878, 881, 882; 602/5, 16, 602/23, 26, 32–40, 12, 20, 13, 60–62; 606/237, 240–242, 345; 5/882, 610, 5/616, 621, 622, 624; 24/170, 515, 498; 297/217.1, 217.3, 284.1, 284.4, 284.8, 297/354.1, 353
See application file for complete search history.

(56) References Cited

U.S. PATENT DOCUMENTS

| 161,323 | A | 3/1875 | Brown |
|---|---|---|---|
| 1,066,190 | A | 7/1913 | Ellingsworth |
| 2,198,908 | A | 4/1940 | Ellis |
| 2,319,400 | A | 5/1943 | Hartmann |
| 2,817,333 | A | 12/1957 | Cole |
| 2,832,334 | A | 4/1958 | Whitelaw |
| 3,477,428 | A | 11/1969 | Hare |
| 3,756,227 | A | 9/1973 | Sager |
| 3,762,405 | A | 10/1973 | De George |
| 3,804,085 | A | 4/1974 | Eshuis |
| 3,906,942 | A | 9/1975 | Lumb, Jr. |
| 4,111,194 | A | 9/1978 | Cox |
| 4,328,794 | A | 5/1982 | Holmes |
| 4,336,796 | A | 6/1982 | Andrews |
| 4,608,971 | A | 9/1986 | Borschneck |
| 4,612,919 | A | 9/1986 | Best |
| 4,657,000 | A | 4/1987 | Hepburn |
| 4,708,131 | A | 11/1987 | Kendrick |
| 4,911,152 | A | 3/1990 | Barnes |
| 5,101,815 | A | 4/1992 | Landon-Orr |
| 5,116,296 | A | 5/1992 | Watkins |
| 5,117,814 | A | 6/1992 | Luttrell |
| 5,162,039 | A | 11/1992 | Dahners |
| 5,387,185 | A | 2/1995 | Johnson, Jr. |

(Continued)

OTHER PUBLICATIONS http://www.medishopsk.sk/xs_downloads/file-36.pdf; Padded Board, Pro, Air, and SAM Splints; Nov. 2010.

(Continued)

*Primary Examiner* — Michael A. Brown
(74) *Attorney, Agent, or Firm* — Neustel Law Offices

(57) ABSTRACT

A fraction splint for providing treatment to a broken or damaged lower extremity which includes a segmented-pole, an ankle assembly having a pad, strap, and retaining assembly, wherein the ankle assembly is retained inwardly of the foot, a groin assembly having a pad, strap, and tensioning assembly extending away from the ankle assembly, and a plurality of cravat straps. The ankle assembly has a curved back plate with upper and lower recesses to permit space for ankle prominences and a double-socket and closed-ended retaining cap for receiving a folded or non-folded end of the segmented-pole. The tensioning assembly includes a back plate, an open-ended intermediary socket, an adjustment assembly, and a retaining cap having a closed-ended socket for receiving the opposite end of the pole. The adjustment assembly is used to move the upper retaining cap towards or away from the back plate to apply traction to the attached leg.

20 Claims, 7 Drawing Sheets

(56) References Cited

U.S. PATENT DOCUMENTS

| | | |
|---|---|---|
| 5,823,931 A | 10/1998 | Gilmour |
| 6,045,520 A | 4/2000 | Buckley |
| 6,394,972 B1 | 5/2002 | Slishman |
| 6,669,659 B2 | 12/2003 | Dittmer |
| 6,913,587 B2 | 7/2005 | Slishman |
| 7,022,094 B2 | 4/2006 | Buckman |
| 7,052,479 B2 | 5/2006 | Drennan |
| 7,507,216 B2 | 3/2009 | Buckman |
| 7,670,308 B2 | 3/2010 | Borschneck |
| 2006/0155232 A1* | 7/2006 | Ceriani .......................... 602/23 |
| 2006/0184083 A1 | 8/2006 | Buckman |

OTHER PUBLICATIONS http://splints.webs.com/; REEL Splint Systems; Nov. 2010.

http://www.lifemedicalsupplier.com/immobilizationextrication-emergency-vacuum-splints-c-16_24.html; Life Medical Supplier; Nov. 2010.

http://www.sagersplints.com/pages/home.html; Minto Research & Development, Inc; Dec. 2010.

http://www.haretractionsplint.com/; Hare Traction; Dec. 2010.

http://www.epandr.com/index.php; Emergency Products + Research; Dec. 2010.

http://www.medicalsearch.com.au/Products/Femoral-Leg-Traction-Splint-CT-6-21848; Faretec; Dec. 2010.

\* cited by examiner

US 8,870,802 B1

TRACTION SPLINT

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to a traction device and more specifically it relates to a traction splint for providing treatment to persons suffering from a broken or damaged lower extremity, such as a mid-shaft femur fracture.

2. Description of the Related Art

Any discussion of the related art throughout the specification should in no way be considered as an admission that such related art is widely known or forms part of common general knowledge in the field.

Traction splint devices have been in use for years to stabilize and apply traction to a person's leg when they are suffering from a broken, fractured, or damaged lower extremity, such as a femur, thigh bone, etc. Prior art traction splints generally fail in that they do not sufficiently stay affixed to the individual during movement, are generally difficult to affix to the lower extremity of the person, and are uncomfortable to wear. In addition, prior art traction splints typically extend past the foot of the patient which leads to difficulties when boarding patients into aircraft, ambulances, or where space is limited. In addition, the extension past the foot of the patient can increase the chances of the traction split being bumped into objects or being caught upon objects or persons while moving, all of which leads to the increase in pain for the patient.

Because of the inherent problems with the related art, there is a need for a new and improved fraction splint for providing treatment to persons suffering from a broken or damaged lower extremity, such as a mid-shaft femur fracture.

BRIEF SUMMARY OF THE INVENTION

A system for providing treatment to persons suffering from a broken or damaged lower extremity, such as a mid-shaft femur fracture. The invention generally relates to a traction device which includes a segmented-pole, an ankle assembly having a pad, strap, and retaining assembly, wherein the ankle assembly is retained inwardly of the foot, a groin assembly having a pad, strap, and tensioning assembly extending away from the ankle assembly, and a plurality of cravat straps. The ankle assembly has a curved back plate with upper and lower recesses to permit space for ankle prominences and a double-socket and closed-ended retaining cap for receiving a folded or non-folded end of the segmented-pole. The tensioning assembly includes a back plate, an open-ended intermediary socket, an adjustment assembly, and a retaining cap having a closed-ended socket for receiving the opposite end of the pole. The adjustment assembly is used to move the upper retaining cap towards or away from the back plate to apply traction to the attached leg.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview.

Figure 1:
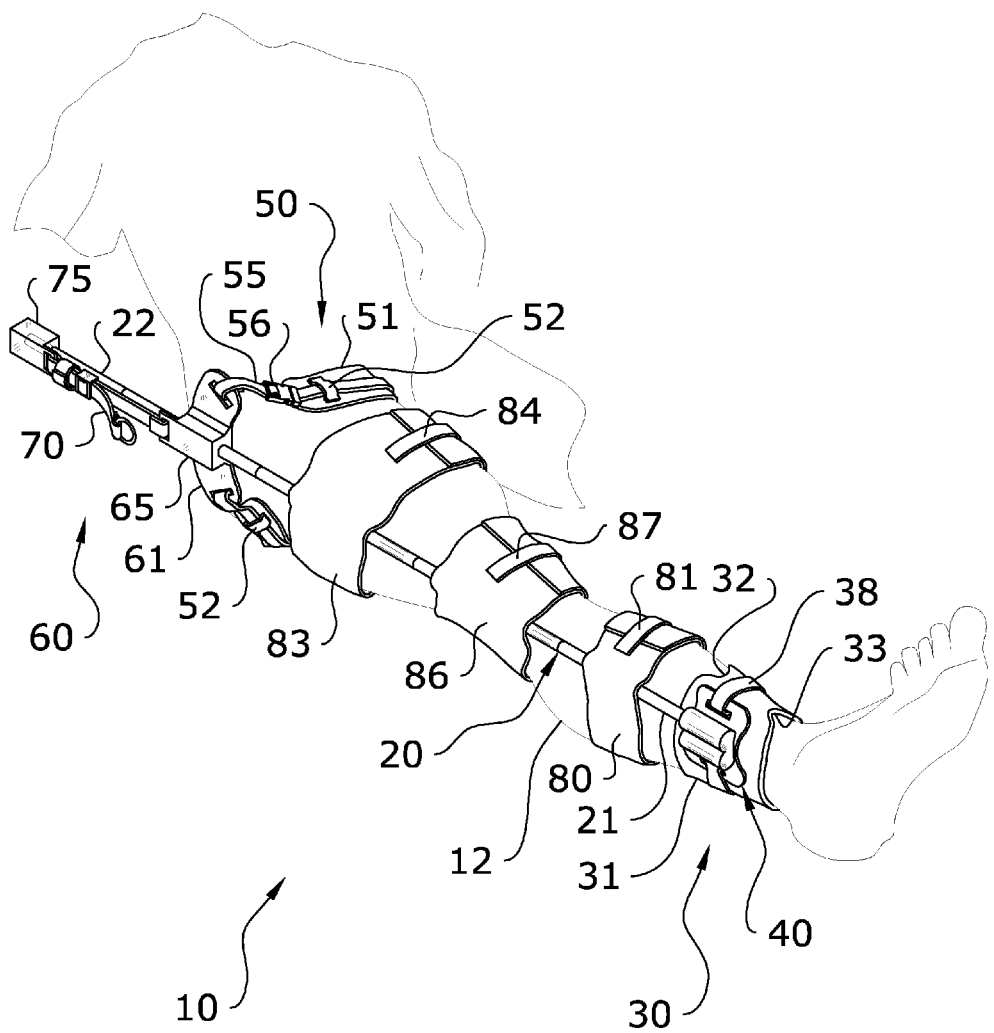
FIG. 1 is an upper perspective view of the present invention attached to the leg of the patient and applying traction, wherein the first end of the pole is in a non-folded position.
Figure 2:
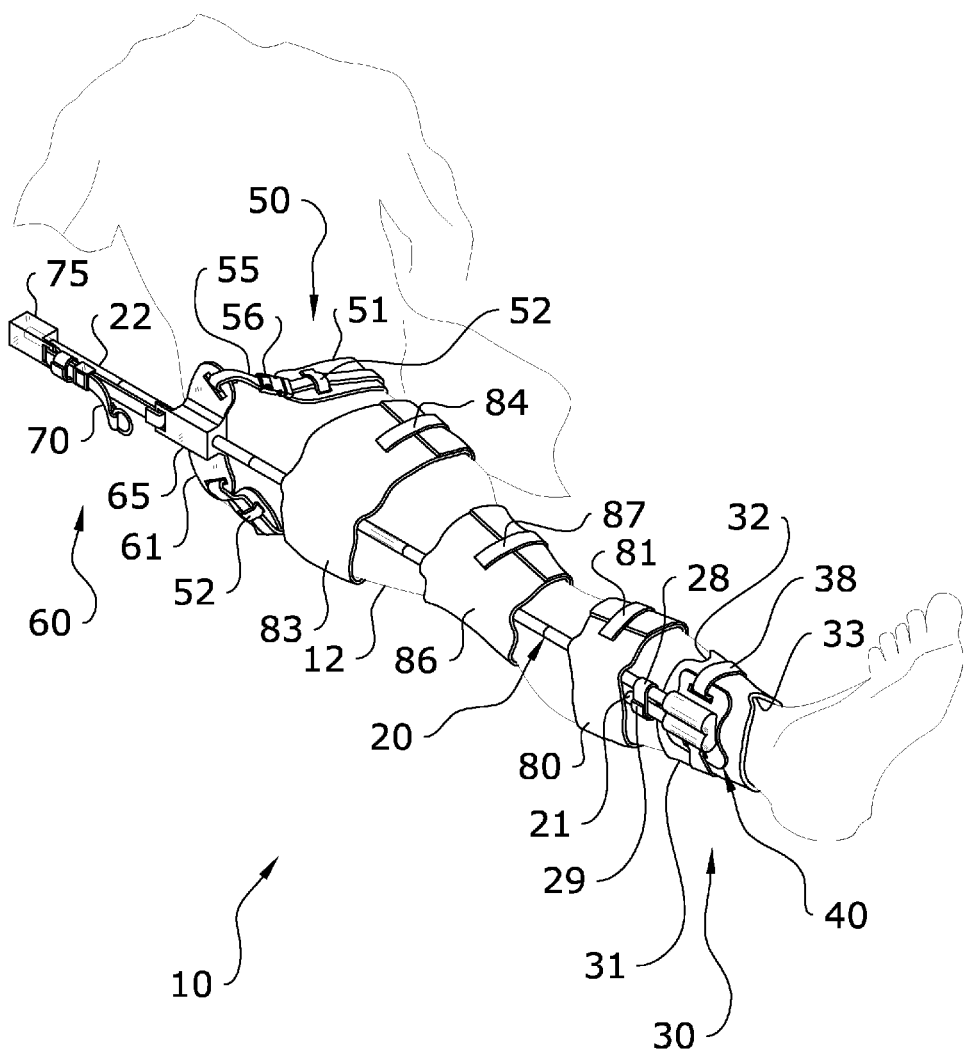
FIG. 2 is an upper perspective view of the present invention attached to the leg of the patient and applying traction, wherein the first end of the pole is in a folded position.
Figure 3:
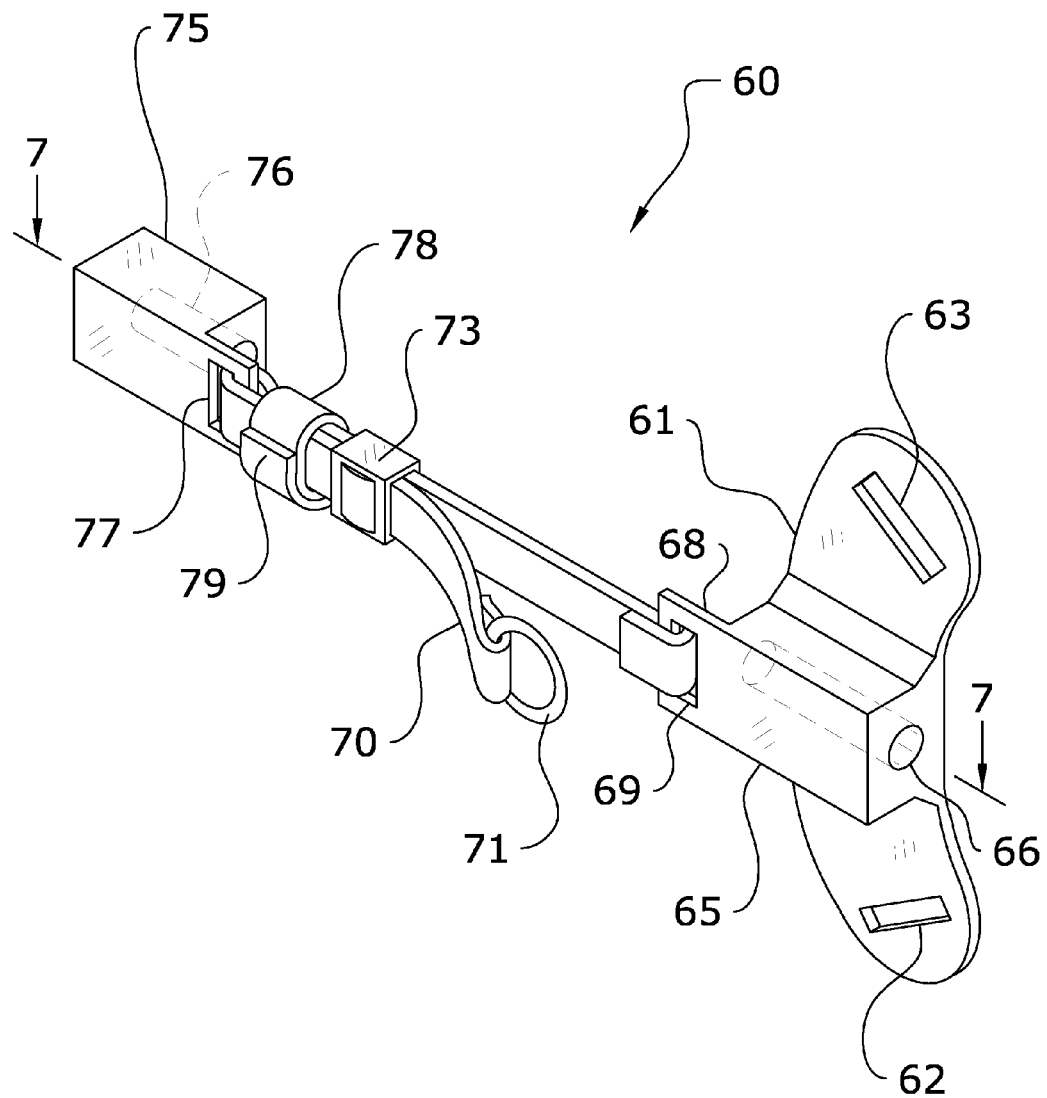
FIG. 3 is an upper perspective view of the tensioning assembly.
Figure 4:
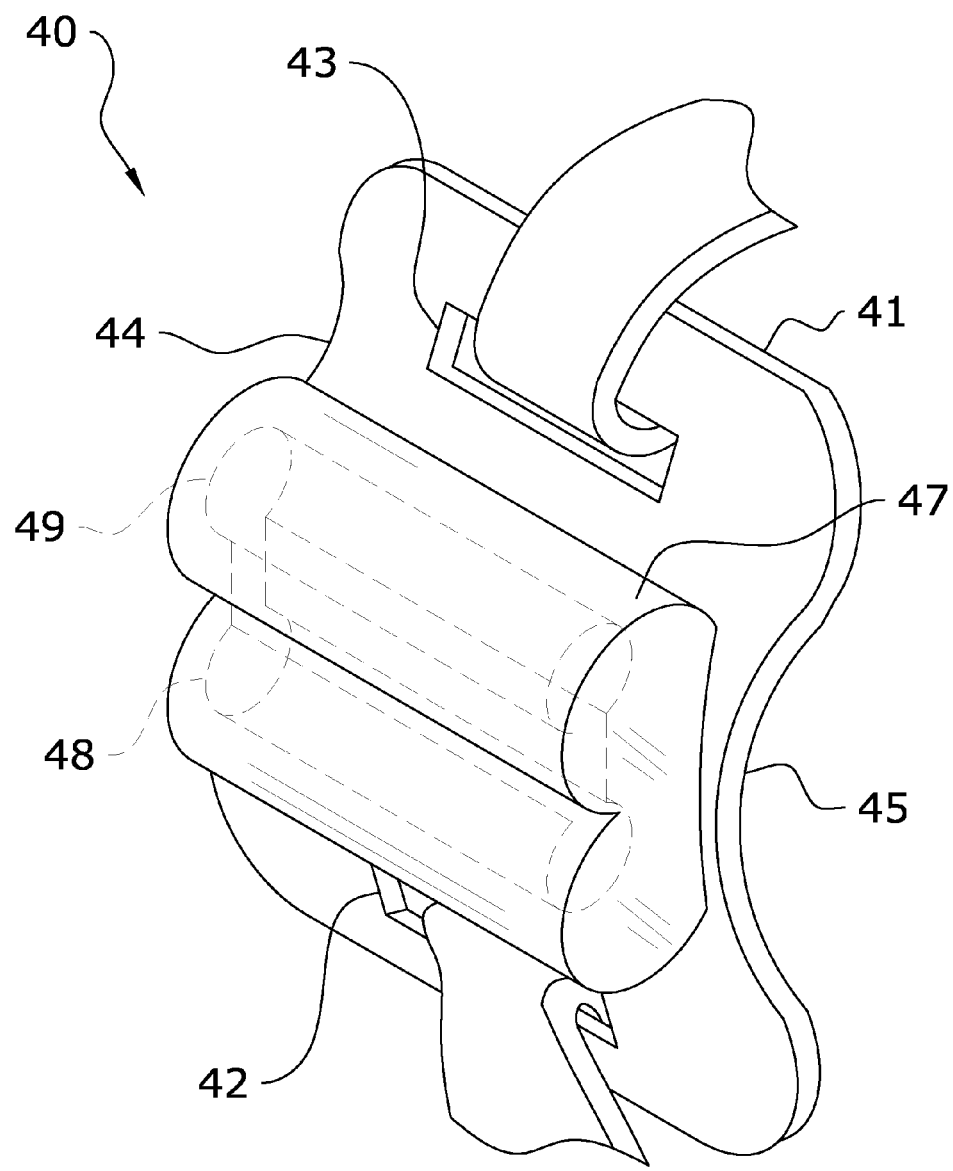
FIG. 4 is an upper perspective view of the retaining assembly connected to the ankle strap.
Figure 5:
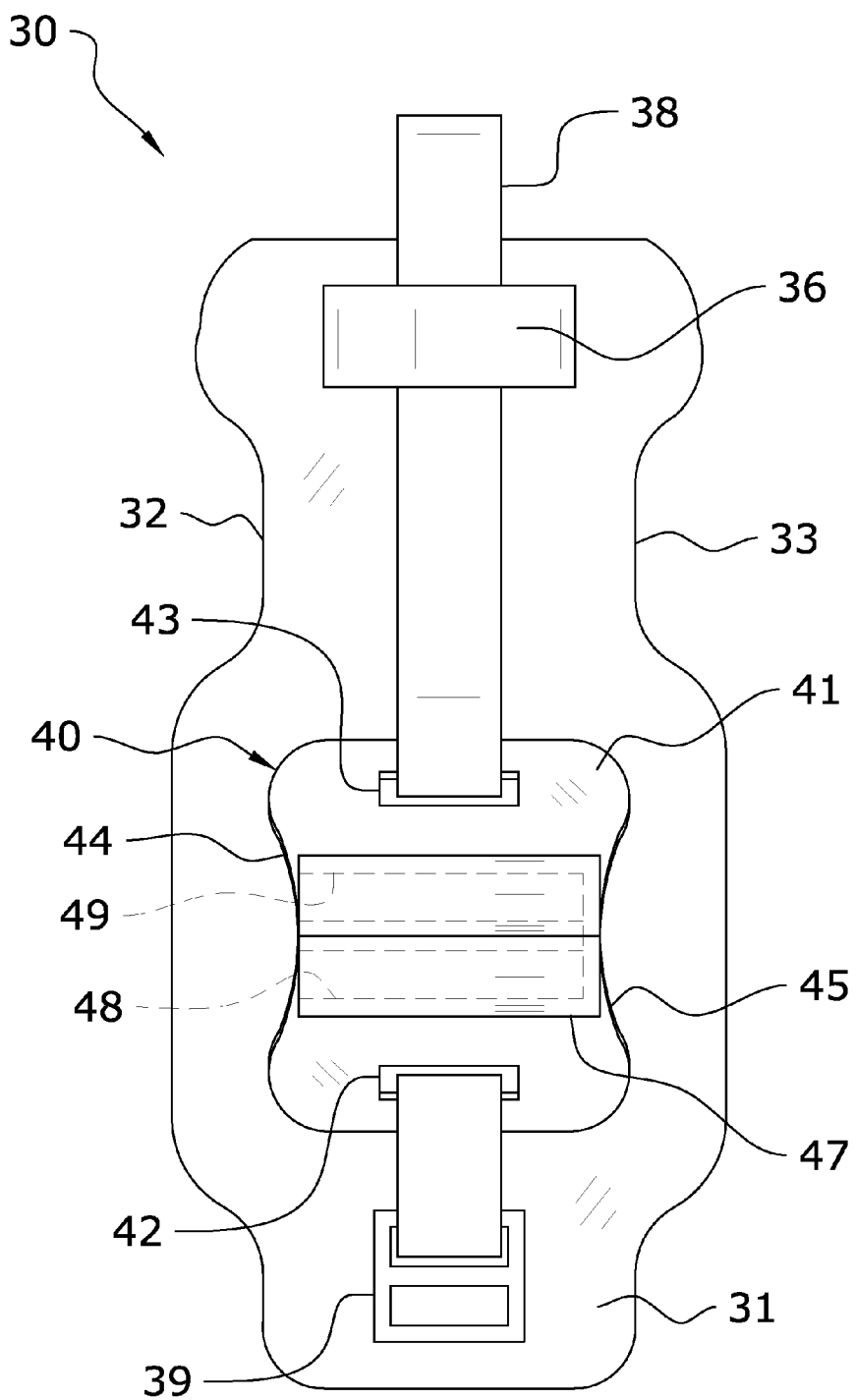
FIG. 5 is a side view of the ankle assembly.
Figure 6:
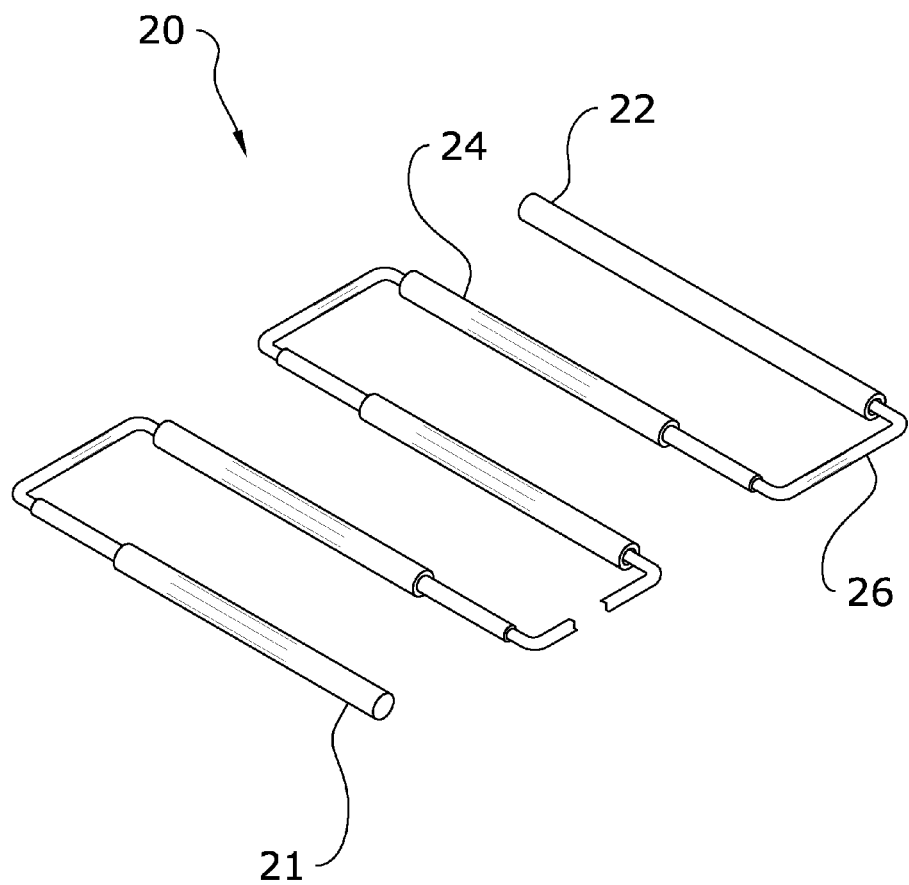
FIG. 6 is an upper perspective view of the pole with the segments separated.
Figure 7:
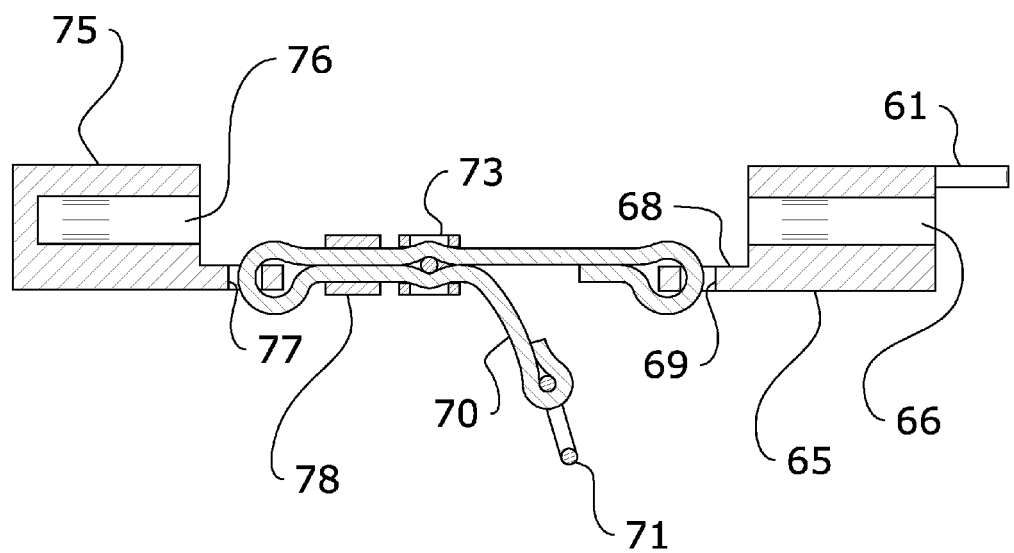
FIG. 7 is a sectional view taken along lines 7-7 of FIG. 3.

Turning now descriptively to the drawings, in which similar reference characters denote similar elements throughout the several views, FIGS. 1 through 7 illustrate a traction splint 10, which comprises a segmented-pole 20, an ankle assembly 30 having a pad 31, strap 38, and retaining assembly 40, wherein the ankle assembly 30 is retained inwardly of the foot, a groin assembly 50 having a pad 51, strap 55, and tensioning assembly 60 extending away from the ankle assembly 30, and a plurality of cravat straps 80, 83, 86. The ankle assembly 30 has a curved back plate 41 with upper and lower recesses 44, 45 to permit space for ankle prominences and a double-socket 48, 49 and closed-ended retaining cap 47 for receiving a folded or non-folded end 21 of the segmented-pole 20. The tensioning assembly 60 includes a back plate 61, an open-ended intermediary socket 66, an adjustment assembly having a strap 70 and buckle 73, and an upper retaining cap 75 having a closed-ended socket 76 for receiving the opposite end 22 of the pole 20. The adjustment assembly is used to move the upper retaining cap 75 towards or away from the back plate 61 to apply traction to the attached leg 12.

B. Segmented-Pole.

The pole 20 is preferably comprised of a plurality of carbon-fiber or aluminum hollow-segments 24 connected via an internal shock elastic cord 26. In this construction, the pole 20 may be doubled at the first end 21 for shortening the overall length of the pole 20 such as to accommodate for different length legs 12. The pole 20 may also be inserted into the end cap 47 in a non-folded manner such as when full extension of the pole 20 is needed. The pole 20 preferably includes an organizer strap 28 adjacent at least the first end 21 for being wrapped around the pole 20 when folded over such as to retain the folded-over portion of the pole 20 together. The organizer strap 28 may include various fasteners 29, such as a hook and loop fastening construction.

C. Ankle Assembly.

The splint 10 includes the ankle assembly 30 for retaining the first end 21 of the pole 20 at the ankle in such a manner as to prevent the first end 21 from moving past or below the foot, wherein the first end 21 is thus retained inwardly of the foot. The ankle assembly 30 generally includes an ankle pad 31, an ankle strap 38, and a retaining assembly 40. The present invention can be applied to the left or right leg, as the ankle assembly 30 is reversible.

The ankle pad 31 is comprised of a padded construction and is for being engaged around the ankle or portion of the leg 12 adjacent the ankle. The ankle pad 31 is comprised of an elongated structure such as to sufficiently wrap around the ankle or lower leg 12 adjacent the ankle. The ankle pad 31 may also be elastic or stretchable. The ankle pad 31 also includes an upper recess 32 and a lower recess 33. In addition, the ankle pad 31 includes one or more receiver loops 36 for receiving the ankle strap 38 therethrough such that the ankle strap 38 parallels the ankle pad 31. The ankle pad 31 may include one or more fasteners to independently secure the ankle pad 31 to the patient.

The ankle strap 38 is comprised of a narrower construction than the ankle pad 31 and extends through the receiver loops 36 and through first and second slots 42, 43 of the back plate 31 of the lower retaining assembly 40. The ankle strap 38 may be comprised of various materials, such as nylon, and the ankle strap 38 generally includes an end fastener 39 such as a buckle to permit for attachment and removal of the ankle strap 38, as well as adjustability of the looped-diametric size of the ankle strap 38.

The retaining assembly 40 is secured upon the ankle pad 31 via the ankle strap 38. The lower retaining assembly 40 includes a back plate 41 having a first slot 42 along a first lateral side of the back plate 41 and a second slot 43 along a second lateral side of the back plate 41. As stated, the first slot 42 and the second slot 43 receive the ankle strap 38. The back plate 41 is also curved in an outward manner between the first and second lateral sides and slots 42, 43 to follow the curved or rounded shape of the ankle or lower portion of the leg 12. The back plate 41 also includes upper and lower curved recesses 44, 45, such that the upper recess 44 along the upper side curves downwardly and the lower recess 45 along the lower side curves upwardly to permit space for the ankle prominence. It is appreciated that having both the upper and lower recesses 44, 45 permits for the ankle assembly 30 to be applied to the left or the right leg 12.

Attached to the back plate 41 is the lower retaining cap 47 for receiving the first end 21 of the pole 20. The cap 47 includes a first socket 48 and a second socket 49 which parallel each other and the lengthwise axis of the leg 12, wherein each of the sockets 48, 49 have an open upper end and a closed lower end such that the first end 21 of the pole 20 is inserted within one or both of the sockets 48, 49 and seated therein. The sockets 48, 49 are interconnected along a length of the sockets 48, 49 which permits for the first end 21 to be folded over and inserted within the first and second sockets 48, 49. When the pole 20 is not folded, such as to utilize the full length of the pole 20, the end of the pole 20 is simply inserted within either one of the first socket 48 or the second socket 49 of the lower retaining cap 47, thus leaving the other socket 48, 49 empty.

D. Groin Assembly.

The splint 10 includes the groin assembly 50 to retain the second end 22 of the pole 20 and to provide for the adjustment of the splint 10 which provides the traction to the leg 12. The groin assembly 50 attaches at the groin or upper leg 12 of the patient and extends upwardly or outwardly therefrom to a point past the groin or near the waist of the patient and away from the ankle assembly 30. The groin assembly 50 generally includes a groin pad 51, a groin strap 55, and a tensioning assembly 60.

The groin pad 51 is comprised of a padded construction and is for being engaged around the groin or upper portion of the leg 12 adjacent the groin and hip. The groin pad 51 is comprised of an elongated structure such as to sufficiently wrap around the leg 12 at the groin. The groin pad 51 may also be elastic or stretchable. The groin pad 51 may include a slight upper or lower recess to provide for a more comfortable wrapping of the groin pad 51 around the leg; however the upper and lower curved recesses of the groin pad 51 generally angle at much less of a degree than the upper and lower recesses of the ankle pad 31 because of the lack of any boney structure (ankle prominences) extending outwardly. The upper and lower recesses permit for the groin pad 51 to be wrapped around either leg 12 while retaining the receiver loops 52 on the outside. In addition, the groin pad 51 includes one or more receiver loops 52 for receiving the groin strap 55 therethrough such that the groin strap 55 parallels the groin pad 51. The groin pad 51 may include one or more fasteners to independently secure the groin pad 51 to the patient.

The groin strap 55 is comprised of a narrower construction than the groin pad 51 and extends through the receiver loops 52 and through first and second slots 62, 63 of the back plate 61 of the tensioning assembly 60. The groin strap 55 may be comprised of various materials, such as nylon, and the groin strap 55 generally includes an end fastener 56 such as a buckle to permit for attachment and removal of the groin strap 55, as well as adjustability of the looped-diametric size of the groin strap 55.

The tensioning assembly 60 is secured upon the groin pad 51 via the groin strap 55. The tensioning assembly 60 includes a back plate 61 having a first slot 62 along a first lateral side of the back plate 61 and a second slot 63 along a second lateral side of the back plate 61. As stated, the first slot 62 and the second slot 63 receive the groin strap 55. The back plate 61 is also curved in an outward manner between the first and second lateral sides and slots 62, 63 to follow the curved or rounded shape of the groin or upper portion of the leg 12. The back plate 61 may include an upper and/or lower curved recess to follow the shape of the groin pad 51. The lower side of the back plate 61 preferably is curved upwardly to follow the radius of the hip.

Attached to the back plate 61 of the tensioning assembly 60 is preferably an intermediate retainer 65 having a socket 66 extending therethrough and open at both ends for permitting passage of the pole 20 therethrough. The intermediate retainer 65 is used to retain the pole 20 in a straight manner along the leg 12 and to provide support for the pole 20 when adjusting the strap 70. Because of the force applied to the pole 20 from adjustment of the strap 70, it is important that the intermediate retainer 65 is located close to but still partially separated from the end 22 of the pole 20. Extending from the intermediate retainer 65 is an extension tab 68 that has a connecting slot 69 for receiving an end of the strap 70.

The adjustment assembly generally comprises the strap 70, buckle 73, and retaining cap 75. The strap 70 extends in a manner to parallel the leg 12 and extends outwardly from the intermediate retainer 65 and back plate 61 in a direction towards the waist or upper body of the patient. The strap 70 is elongated and loops through a connecting slot 77 in the retaining cap 75 and is retained at a preferred length via being threaded through the buckle 73, which also permits adjustment of the strap 70. The distal end of the strap 70 has an end ring 71, such as a D-shaped ring, secured thereon which serves as a handle or means for pulling upon the strap 70 when tightening the strap 70 and applying traction to the leg 12. Other tightening and loosening mechanisms may be used in place of the buckle 73 as appreciated.

As stated, attached to the strap 70 is the retaining cap 75 via the connecting slot 77. The retaining cap 75 has a socket 76 for receiving the second end 22 of the pole 20. The socket 76 parallels the lengthwise axis of the leg 12, and the socket 76 has an open lower end and a closed upper end such that the second end 22 of the pole 20 is inserted within the socket 76 and seated therein. The retaining cap 75 may also include an organizer strap 78 having hook and loop fasteners 79 to secure the pole 20 there along.

E. Cravat Straps.

The splint 10 also includes a plurality of cravat straps 80, 83, 86 to encircle the pole 20 and the leg 12 thus retaining the pole 20 straight along the length of the leg 12. The cravat straps 80, 83, 86 are generally comprised of a soft, flexible, and possibly elastic construction and each of the cravat straps 80, 83, 86 generally includes its own fastening construction 81, 84, 87, such as hooks and loops, to permit for each cravat strap 80, 83, 86 to be independently secured around the pole 20 and leg 12 at the preferred location. In the preferred embodiment, the splint 10 includes a shin cravat strap 80 to be wrapped around the leg 12 and pole 20 at the shin of the leg 12, a thigh cravat strap 83 to be wrapped around the leg 12 and pole 20 at the lower thigh of the leg 12, and a knee cravat strap 86 to be wrapped around the leg 12 and pole 20 at the knee of the leg 12.

F. Operation of Preferred Embodiment.

In use, the ankle assembly 30 is secured to the lower leg 12, just above the ankle prominence and the groin assembly 50 is secured around the leg 12, just below the hip and groin. The pole 20 is then fed through the intermediate retainer 65 and seated into the socket 48 or 49 of the lower retaining cap 47. The upper end 22 of the pole 20 is also seated within the socket 76 of the upper retaining cap 75 and the adjustment strap 70 is left long to provide slack when inserting the pole 20 into the upper and lower retaining caps 47, 75. If necessary, the first end 21 of the pole 20 is folded-over upon itself to shorten the length of the pole 20 and seated into the first and second sockets 48, 49 of the lower retaining cap 47. The organizer strap 28 is then used to secure the extra pole 20 length to the main pole 20. The knee cravat strap 86 is then secured around the knee and pole 20 to prevent pole 20 deflection while applying traction.

Traction is applied by pulling on the end ring 71 of the adjustment strap 70 which causes the pole 20 to be forced towards the ankle. Traction is held in place by the buckle 73 attached to the strap 70. After the desired amount of traction is applied, the thigh and shin cravat straps 80, 83 are positioned in respective locations around the leg 12 and secured around thereof via the fasteners 81, 84. To lessen the amount of applied fraction, the buckle 73 may be manipulated by applying an outward force to the tab of the buckle 73 to permit the strap 70 to loose and the pole 20 to move away from the ankle.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A traction splint, comprising:
a pole having a first end and a second end;
an ankle strap engaged around the ankle of a patient;
a first retaining cap connected to said ankle strap, said first retaining cap retains said first end of said pole such that said first end of said pole is retained inwardly of the foot of the patient such as to not extend past the foot;
a groin strap engaged around the leg at the groin of the patient; and
a tensioning harness assembly extending from said groin strap, said tensioning harness assembly having an adjustment strap, a buckle, and a second retaining cap, said adjustment strap extends outwardly from said groin strap away from said ankle strap and being adjustable in length via said buckle, said second retaining cap extends outwardly from said buckle, wherein said second retaining cap retains said second end of said pole such that said second retaining cap is adjusted along a length of the leg of the patient to apply traction via adjustment of said adjustment strap relative said buckle;
wherein said pole is comprised of a segmented construction such that said segments of said pole being connected within an internal elastic cord and adapted for being at least partially folded-over upon itself at a respective end for adjusting a total length between said first end and said second end.

2. The traction splint of claim 1, wherein said first retaining cap has a first socket with a closed-lower end such that restricts passage of said first end of said pole and wherein said second retaining cap has a second socket with a closed-upper end such that restricts passage of said second end of said pole.

3. The traction splint of claim 2, wherein said tensioning harness assembly has an intermediate retainer with an open-ended intermediate socket located adjacent said groin strap, said intermediate socket receives said pole therethrough.

4. The traction splint of claim 3, wherein said tensioning harness assembly has a back plate, said back plate having a first slot along a first lateral side of said back plate and a second slot along a second lateral side of said back plate, said first slot and said second slot receive said groin strap, and wherein said back plate curves outwardly between said first lateral side and said second lateral side, wherein said intermediate retainer is attached to said back plate and wherein said adjustment strap extends from said back plate.

5. The traction splint of claim 1, wherein said first retaining cap comprises a first closed-end socket and a second closed-end socket, said first closed-end socket and said second closed-end socket being interconnected to receive said folded-over first end of said segmented pole.

6. The fraction splint of claim 1, wherein said first retaining cap is connected to a back plate, said back plate having a first slot along a first lateral side of said back plate and a second slot along a second lateral side of said back plate, said first slot and said second slot receive said ankle strap, and wherein said back plate curves outwardly between said first lateral side and said second lateral side.

7. The fraction splint of claim 6, wherein said back plate has an upper side and a lower side, wherein said upper side curves downwardly and wherein said lower side curves upwardly.

8. The fraction splint of claim 1, including an ankle pad and a groin pad, said ankle strap encircles said ankle pad and said groin strap encircles said groin pad.

9. The fraction splint of claim 1, including a plurality of cravat straps encircling said pole and the leg.

10. The fraction splint of claim 9, wherein said plurality of cravats include a shin cravat, a thigh cravat, and a knee cravat.

11. A traction splint, comprising:
a pole having a first end and a second end;
wherein said pole is comprised of a segmented construction such that said segments of said pole being connected within an internal elastic cord and adapted for being at least partially folded-over upon itself at a respective end for adjusting a total length between said first end and said second end;
an ankle strap engaged around the ankle of a patient;
a first retaining cap connected to said ankle strap, said first retaining cap retains said first end of said pole such that said first end of said pole is retained inwardly of the foot of the patient such as to not extend past the foot;
wherein said first retaining cap comprises a first closed-end socket and a second closed-end socket, said first closed-end socket and said second closed-end socket being interconnected along a length of said sockets such as to receive a folded-over said first end of said segmented pole within both of said closed-end sockets or a non folded-over said first end within one of either said closed-end sockets;
a groin strap engaged around the leg at the groin of the patient; and
a tensioning harness assembly extending from said groin strap, said tensioning harness assembly having an adjustment strap, a buckle, and a second retaining cap, said adjustment strap extends outwardly from said groin strap away from said ankle strap and being adjustable in length via said buckle, said second retaining cap extends outwardly from said buckle, wherein said second retaining cap retains said second end of said pole such that said second retaining cap is adjusted along a length of the leg of the patient to apply traction via adjustment of said adjustment strap relative said buckle;
wherein said second retaining cap has a socket with a closed-upper end such that restricts passage of said second end of said pole therethrough.

12. The traction splint of claim 11, wherein said tensioning harness assembly has an open-ended intermediate socket located adjacent said groin strap, said intermediate socket receives said pole therethrough.

13. The fraction splint of claim 12, wherein said tensioning harness assembly has a back plate, said back plate having a first slot along a first lateral side of said back plate and a second slot along a second lateral side of said back plate, said first slot and said second slot receive said groin strap, and wherein said back plate curves outwardly between said first lateral side and said second lateral side, wherein said intermediate socket is attached to said back plate and wherein said adjustment strap extends from said back plate.

14. The traction splint of claim 11, wherein said first retaining cap is connected to a back plate, said back plate having a first slot along a first lateral side of said back plate and a second slot along a second lateral side of said back plate, said first slot and said second slot receive said ankle strap, and wherein said back plate curves outwardly between said first lateral side and said second lateral side.

15. The traction splint of claim 14, wherein said back plate has an upper side and a lower side, wherein said upper side curves downwardly and wherein said lower side curves upwardly.

16. The traction splint of claim 11, including an ankle pad and a groin pad, said ankle strap encircles said ankle pad and said groin strap encircles said groin pad.

17. The fraction splint of claim 11, including a plurality of cravat straps encircling said pole and the leg.

18. The fraction splint of claim 17, wherein said plurality of cravats include a shin cravat, a thigh cravat, and a knee cravat.

19. A traction leg splint, comprising:
a pole having a first end and a second end;
wherein said pole is comprised of a segmented construction such that said segments of said pole being connected within an internal elastic cord and adapted for being at least partially folded-over upon itself at a respective end for adjusting a total length between said first end and said second end;
an ankle pad engaged around an ankle of a patient;
an ankle strap encircling said ankle pad;
a first back plate having a first slot along a first lateral side of said first back plate and a second slot along a second lateral side of said first back plate, said first slot and said second slot of said first back plate receive said ankle strap, and wherein said first back plate curves outwardly between said first lateral side and said second lateral side;
wherein said first back plate has an upper side and a lower side, wherein said upper side curves downwardly and wherein said lower side curves upwardly;
a first retaining cap connected to said first back plate, said first retaining cap retains said first end of said pole such that said first end of said pole is retained inwardly of the foot of the patient such as to not extend past the foot;
wherein said first retaining cap comprises a first closed-end socket and a second closed-end socket, said first closed-end socket and said second closed-end socket being interconnected along a length of said sockets such as to receive a folded-over said first end of said segmented pole within both of said closed-end sockets or a non folded-over said first end within one of either said closed-end sockets;
a groin pad engaged around a leg at the groin of the patient;
a groin strap encircling said groin pad;
a tensioning harness assembly extending from said groin strap, said tensioning harness assembly having a second back plate, an open-ended intermediate socket, an adjustment strap, a buckle, and a second retaining cap;
wherein said second back plate has a first slot along a first lateral side of said second back plate and a second slot along a second lateral side of said second back plate, said first slot and said second slot of said second back plate receive said groin strap, and wherein said second back plate curves outwardly between said first lateral side and said second lateral side of said second back plate, wherein said open-ended intermediate socket is connected to said second back plate to receive said pole therethrough;

wherein said adjustment strap extends outwardly from said second back plate away from said ankle strap and being adjustable in length via said buckle;

wherein said second retaining cap extends outwardly from said buckle, wherein said second retaining cap retains said second end of said pole such that said second retaining cap is adjusted along a length of the leg of the patient to apply traction via adjustment of said adjustment strap relative said buckle;

wherein said second retaining cap has a socket with a closed-upper end such that restricts passage of said second end of said pole therethrough; and a plurality of cravat straps encircling said pole and the leg.

20. A traction splint, comprising:

a pole having a first end and a second end;

an ankle strap engaged around the ankle of a patient;

a first retaining cap connected to said ankle strap, said first retaining cap retains said first end of said pole such that said first end of said pole is retained inwardly of the foot of the patient such as to not extend past the foot;

a groin strap engaged around the leg at the groin of the patient; and a tensioning harness assembly extending from said groin strap, said tensioning harness assembly having an adjustment strap, a buckle, and a second retaining cap, said adjustment strap extends outwardly from said groin strap away from said ankle strap and being adjustable in length via said buckle, said second retaining cap extends outwardly from said buckle, wherein said second retaining cap retains said second end of said pole such that said second retaining cap is adjusted along a length of the leg of the patient to apply traction via adjustment of said adjustment strap relative said buckle;

wherein said first retaining cap has a first socket with a closed-lower end such that restricts passage of said first end of said pole and wherein said second retaining cap has a second socket with a closed-upper end such that restricts passage of said second end of said pole;

wherein said tensioning harness assembly has an intermediate retainer with an open-ended intermediate socket located adjacent said groin strap, said intermediate socket receives said pole therethrough.

* * * * *